(12) United States Patent
Spanyer

(10) Patent No.: US 11,278,298 B2
(45) Date of Patent: Mar. 22, 2022

(54) DECOMPRESSION DEVICE AND METHOD

(71) Applicant: Jonathon Spanyer, Cleves, OH (US)

(72) Inventor: Jonathon Spanyer, Cleves, OH (US)

( * ) Notice: Subject to any disclaimer, the term of this patent is extended or adjusted under 35 U.S.C. 154(b) by 225 days.

(21) Appl. No.: 16/445,519

(22) Filed: Jun. 19, 2019

(65) Prior Publication Data

US 2020/0397449 A1 Dec. 24, 2020

(51) Int. Cl.
*A61B 17/74* (2006.01)
*A61B 17/16* (2006.01)
*A61M 1/00* (2006.01)
*A61B 17/22* (2006.01)
*A61B 17/88* (2006.01)
*A61F 2/46* (2006.01)

(52) U.S. Cl.
CPC ........ *A61B 17/164* (2013.01); *A61B 17/1664* (2013.01); *A61M 1/0023* (2013.01); *A61B 17/1659* (2013.01); *A61B 17/8897* (2013.01); *A61B 2017/22038* (2013.01); *A61F 2002/4685* (2013.01); *A61M 2202/10* (2013.01); *A61M 2210/02* (2013.01)

(58) Field of Classification Search
CPC ............ A61B 17/74–748; A61B 17/16; A61B 17/1635–1642
See application file for complete search history.

(56) References Cited

U.S. PATENT DOCUMENTS

| | | | |
|---|---|---|---|
| 5,895,351 A | 4/1999 | Nottage et al. | |
| 5,951,561 A * | 9/1999 | Pepper | A61B 17/1717 606/80 |
| 6,197,031 B1 | 3/2001 | Barrette et al. | |
| 6,783,532 B2 | 8/2004 | Steiner et al. | |
| 8,790,321 B2 | 7/2014 | Segina et al. | |

(Continued)

OTHER PUBLICATIONS

Shane A Barwood Jeremy L Wilson Rowan R Molnar & Peter F M Choong, The incidence or acute cardiorespiratory and vascular dysfunction following intramedullary nail fixation of femoral metastasis, Acta Orthopaedica Scandinavica, 71:2, 147-152, DOI:10.1080/000164700317413111.

(Continued)

*Primary Examiner* — Eduardo C Robert
*Assistant Examiner* — Michelle C Eckman
(74) *Attorney, Agent, or Firm* — Argus Intellectual Enterprise; Jordan Sworen; Daniel Enea

(57) ABSTRACT

A decompression device and method for removing marrow and other fluid from an intramedullary canal. The decompression device includes a cannula having a channel that allows fatty marrow to pass therethrough. A first port extends from the device and is in operable connection to a vacuum source that creates suction for removing fluid from the intramedullary canal. In some embodiments, one or more fenestrations are disposed along the second end of the cannula to expedite the removal of the fluid. In operation, the cannula is inserted into the intramedullary canal of a femur. Once fatty marrow is removed from the intramedullary canal, the cannula is removed and a reaming device is inserted into the femur. In this way, the fatty marrow is removed prior to the reaming procedure in order to prevent these fluids from traveling to the lungs causing blockage that leads to severe cardiorespiratory and vascular dysfunction.

16 Claims, 8 Drawing Sheets

(56) References Cited

U.S. PATENT DOCUMENTS

| | | | |
|---|---|---|---|
| 8,845,648 B2 | 9/2014 | Guzman et al. | |
| 8,961,516 B2 | 2/2015 | Nelson et al. | |
| 2003/0097133 A1* | 5/2003 | Green | A61B 17/1617 |
| | | | 606/80 |
| 2007/0276352 A1 | 11/2007 | Crocker et al. | |
| 2018/0000505 A1* | 1/2018 | Onuma | A61B 17/56 |
| 2020/0100800 A1* | 4/2020 | Seykora | A61B 17/1615 |

OTHER PUBLICATIONS

Shane A Barwood Jeremy L Wilson Rowan R Molnar & Peter F M Choong, The incidence of acute cardiorespiratory and vascular dysfunction following intramedullary nail fixation of femoral metastasis, Acta Orthopaedica Scandinavica, 71:2, 147-152, DOI:10.1080/000164700317413111.

* cited by examiner

DECOMPRESSION DEVICE AND METHOD

BACKGROUND OF THE INVENTION

The present invention relates to a device for bone repair surgical procedures. The present invention further provides a method of using the decompression device during a hip fracture repair procedure.

Hip fractures are typically repaired utilizing metal bone reconstruction rods inserted and secured to an existing femur. This procedure requires an orthopedic surgeon to access the intramedullary canal of the femur and ream or widen the interior area of the canal in order to create a space to receive the reconstruction rod. Once the reconstruction rod is received within the intramedullary canal, the orthopedic surgeon nails or otherwise affixes the reconstruction rod into the space for bone reconstruction. In some instances, complications may occur whereby the pressure on the fatty marrow or fluid in the interior space of the canal created during the reaming and nailing procedure forces this fluid out of the canal and into the venous system of the patient. The fluid is then carried to the lungs of the patient. The presence of the substances within the fluid and fatty marrow in the lungs can cause blockage leading to severe cardiorespiratory and vascular dysfunction (CRVD) which may result in negative patient outcomes, including death.

Existing devices provide apparatuses and methods for removing material from the intramedullary cavity using combination reamer-irrigator-aspirator (RIA) devices. During this procedure these RIA devices create additional pressure within the intramedullary cavity. This pressure is believed to be caused by the reamer engaging the marrow and cancellous matrix. These devices combine reaming, irrigating and aspiration into one tool and therefore do not allow for the device, or a method thereof, to perform a decompression of fatty marrow prior to the reaming procedure. Reaming is known to create the largest rise in pressure in the intramedullary canal. By performing the reaming procedure prior to or during decompression, the fatty marrow contents may still be forced out of the interior space of the canal due to the increase in intramedullary cavity. There is currently no priming device, or method thereof, that provides for the decompression of the intramedullary canal prior to the reaming. Additionally, the conventional RIA devices cannot perform this step separately from the reaming, as it combines reaming and decompression. Thus, the undesired effect of CRVD is not prevented through the use of these devices or methods. The RIA devices are specialized tools that are expensive and require assembly before use. These RIA devices include a reaming tip that generally oscillates or rotates to engage the marrow and cancellous matrix. The RIA devices remove bone during the reaming process and cannot be adapted to target specific tissue within the intramedullary canal.

The present invention provides a decompression device that is configured to decrease the amount of fatty marrow in the intramedullary canal which is accessible to a patient's circulatory system as a result of the surgical procedure for bone reconstruction to repair a hip fracture. The fatty marrow includes embolic particles, vasoactive, inflammatory, and thrombogenic substances. The decompression device of the present invention is inserted into the intramedullary canal along the length of a guide wire and activated to remove fat and marrow content from the canal. The device includes an elongated cannula having multiple ports and a handle disposed on a first end thereof. The ports are connectable to vacuum and irrigation sources to facilitate the removal of the fluid in the canal. The cannula terminates at a second end having an open tip thereon. In some embodiments, the cannula includes one or more fenestrations disposed therealong to allow for more efficient removal of the intramedullary fluid and contents.

As the fatty marrow and fluid is removed, the area becomes adequately decompressed. The orthopedic surgeon removes the cannula after the decompression and completes reaming of the femoral canal with a reaming device, a drill inserted along the guide wire. A cannulated femoral reconstruction rod is then disposed over the guide wire, wherein the rod is nailed into position. The guide wire can then be removed and the repair procedure completed. The removal of the fat and marrow content via the decompression device lessens the risk of the patient suffering from cardiorespiratory and vascular dysfunction that can occur when fluid from the intramedullary canal is absorbed into the lungs via the venous system. The present invention provides a device and method for achieving decompression in the intramedullary cavity prior to the reaming and femoral nail installation process that takes place during hip fracture repair procedures. Therefore, incidences of CRVD and post-surgical complications will ideally be reduced using the present invention.

In light of the devices disclosed in the known art, it is submitted that the present invention substantially diverges in design elements and methods from the known art and consequently it is clear that there is a need in the art for an improvement for performing bone repair procedures. In this regard the instant invention substantially fulfills these needs.

SUMMARY OF THE INVENTION

In view of the foregoing disadvantages inherent in the known types of decompression devices and methods now present in the known art, the present invention provides a new decompression device and method wherein the same can be utilized during a hip fracture repair procedure.

In one embodiment of the invention, the decompression device includes a cannula having a channel in fluid communication with a first and a second end, allowing fatty marrow to pass therethrough. A first port extends from the first end of the decompression device and is in operable connection to a vacuum source that creates suction (negative pressure) for removing fluid from the intramedullary canal. In some embodiments, one or more fenestrations are disposed along the second end of the cannula to expedite the removal of the fluid within the intramedullary canal. In operation, the cannula is inserted into the intramedullary canal of a femur. Once fatty marrow is removed from the intramedullary canal, the cannula is removed and a reaming device is inserted into the femur. In this way, the fatty marrow is removed prior to the reaming procedure in order to prevent these fluids from entering the vascular system and traveling to the lungs causing blockage that leads to severe cardiorespiratory and vascular dysfunction.

In operation of the decompression device, the cannula is inserted into the intramedullary canal of a femur. Once fatty marrow is removed from the intramedullary canal, the cannula is removed and a reaming device is inserted into the femur. In this way, the fatty marrow is removed prior to the reaming procedure in order to prevent these fluids from traveling to the lungs causing blockage that leads to severe cardiorespiratory and vascular dysfunction.

It is an objective of the present invention to provide in some embodiments, the decompression device includes a heating element adapted to apply heat and further facilitate decompression.

It is another objective of the present invention to provide an embodiment comprising an ultrasonic transducer for facilitating the fatty marrow to pass through the fenestrations or another opening disposed on the cannula.

It is therefore an object of the present invention to provide a new and improved decompression device and method that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

Figure 3A:
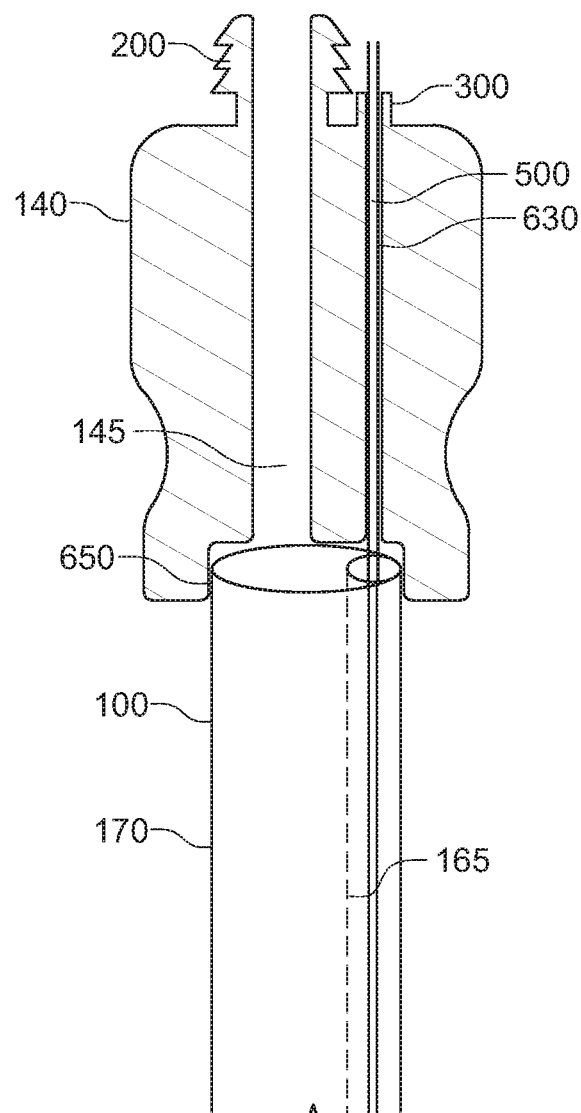

FIG. 3A a side cross sectional view of a second alternate embodiment of the handle and upper end of the cannula of the decompression device.

Figure 3B:
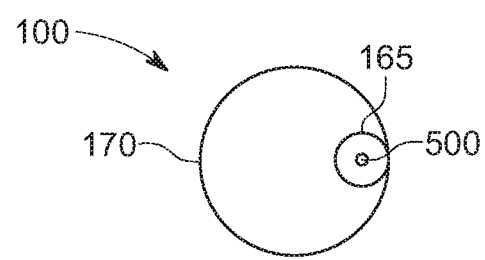

FIG. 3B shows a cross sectional view of the cannula of 3A.

Figure 4A:
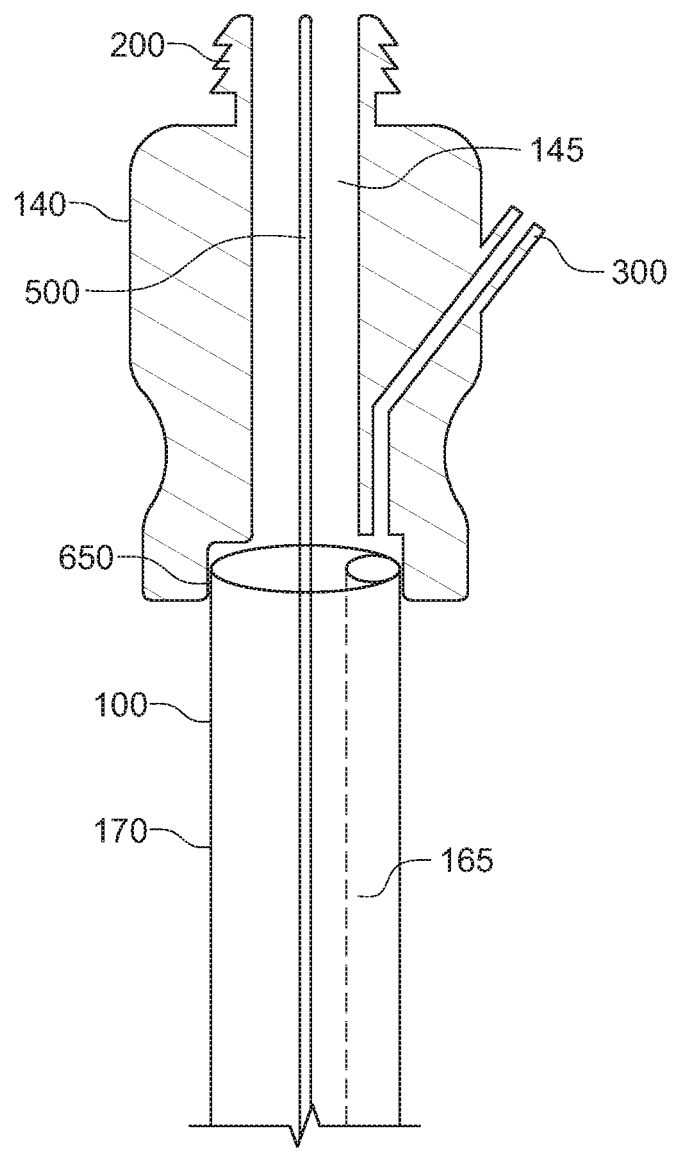

FIG. 4A a side cross sectional view of a third alternate embodiment of the handle and upper end of the cannula of the decompression device.

Figure 4B:
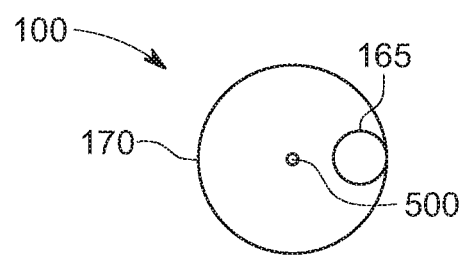

FIG. 4B shows a cross sectional view of the cannula of 4A.

Figure 5:
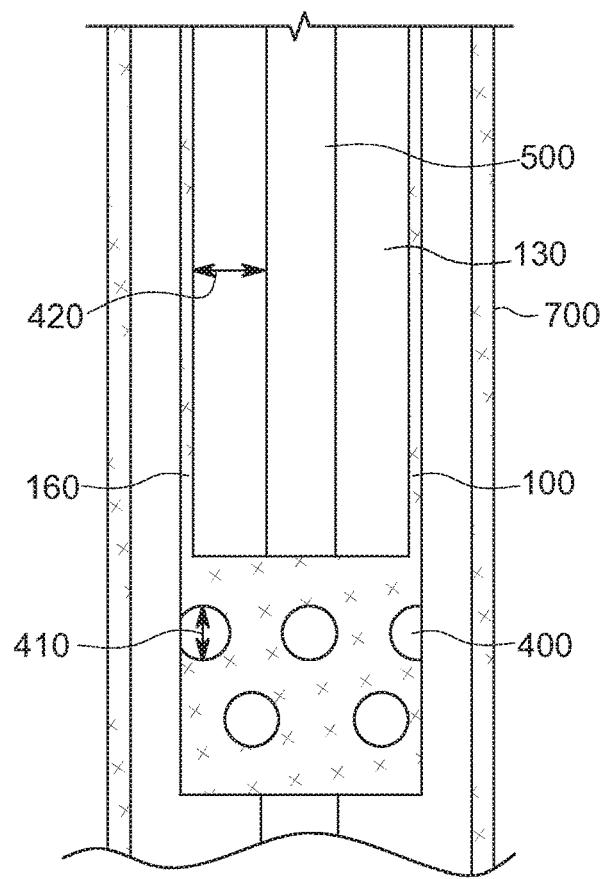

FIG. 5 shows a cross sectional view of a second end of an embodiment of the decompression device inserted into a femur.

Figure 6:
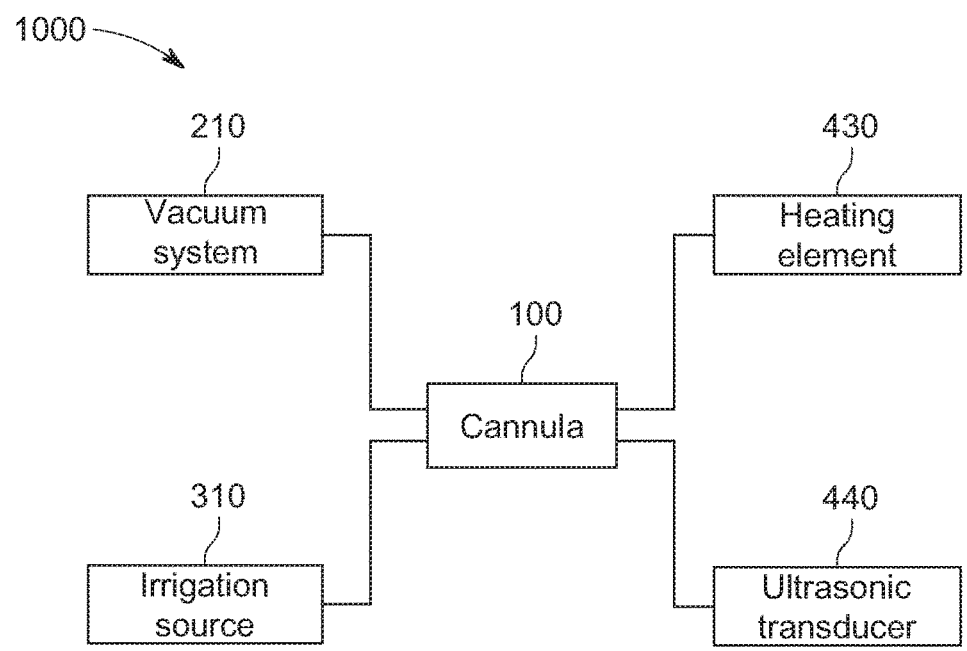

FIG. 6 shows a perspective view of an embodiment of the decompression device inserted through a proximal end of a femur.

Figure 7A:
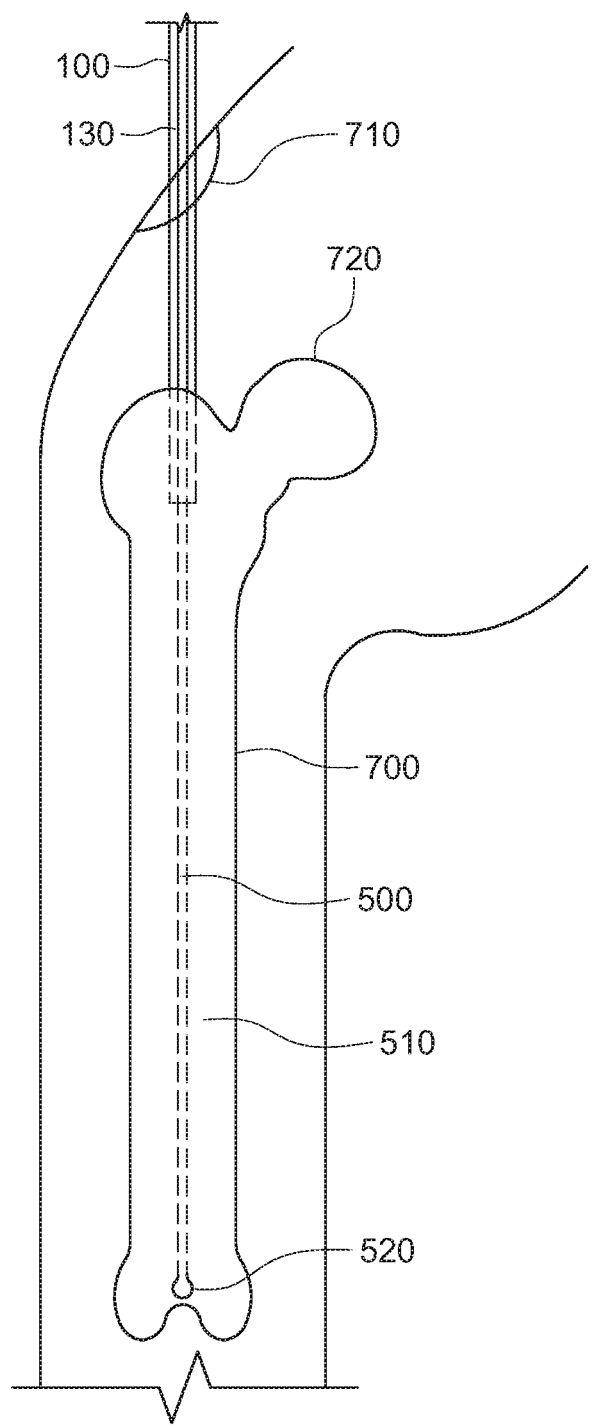

FIG. 7A shows a perspective view of an embodiment of the decompression device inserted into a femur over a guide wire.

Figure 7B:
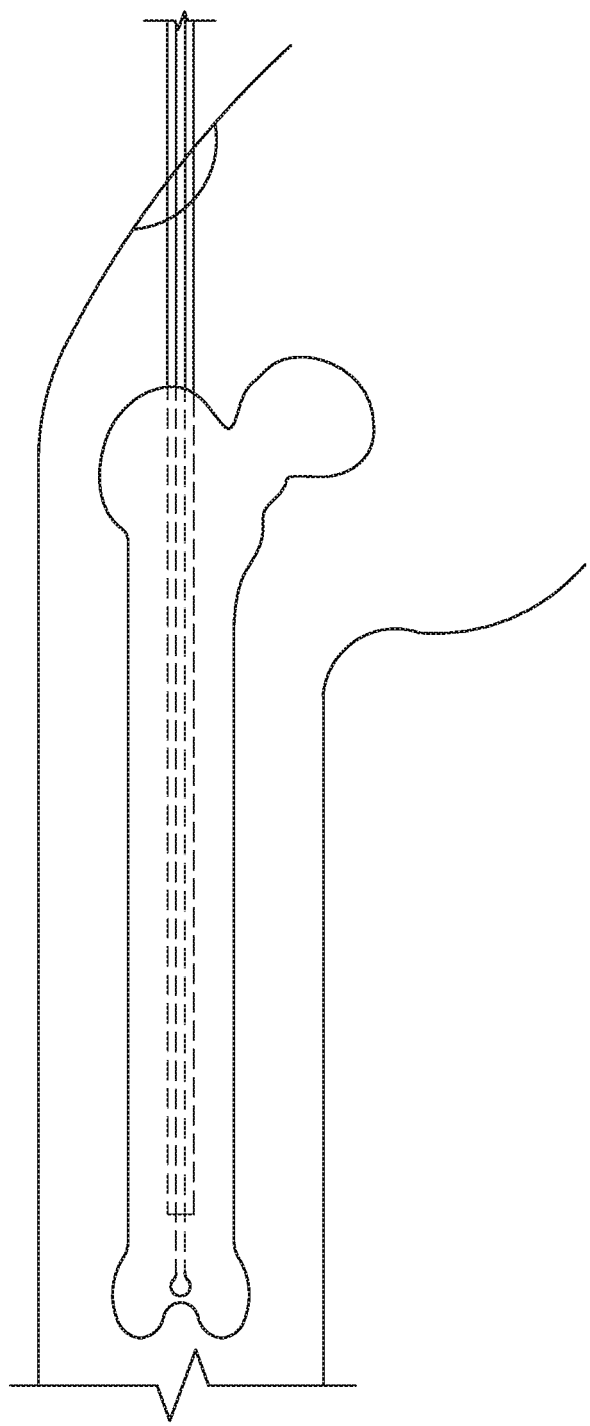

FIG. 7B shows a block diagram of the components of an embodiment of the decompression device.

Figure 8:
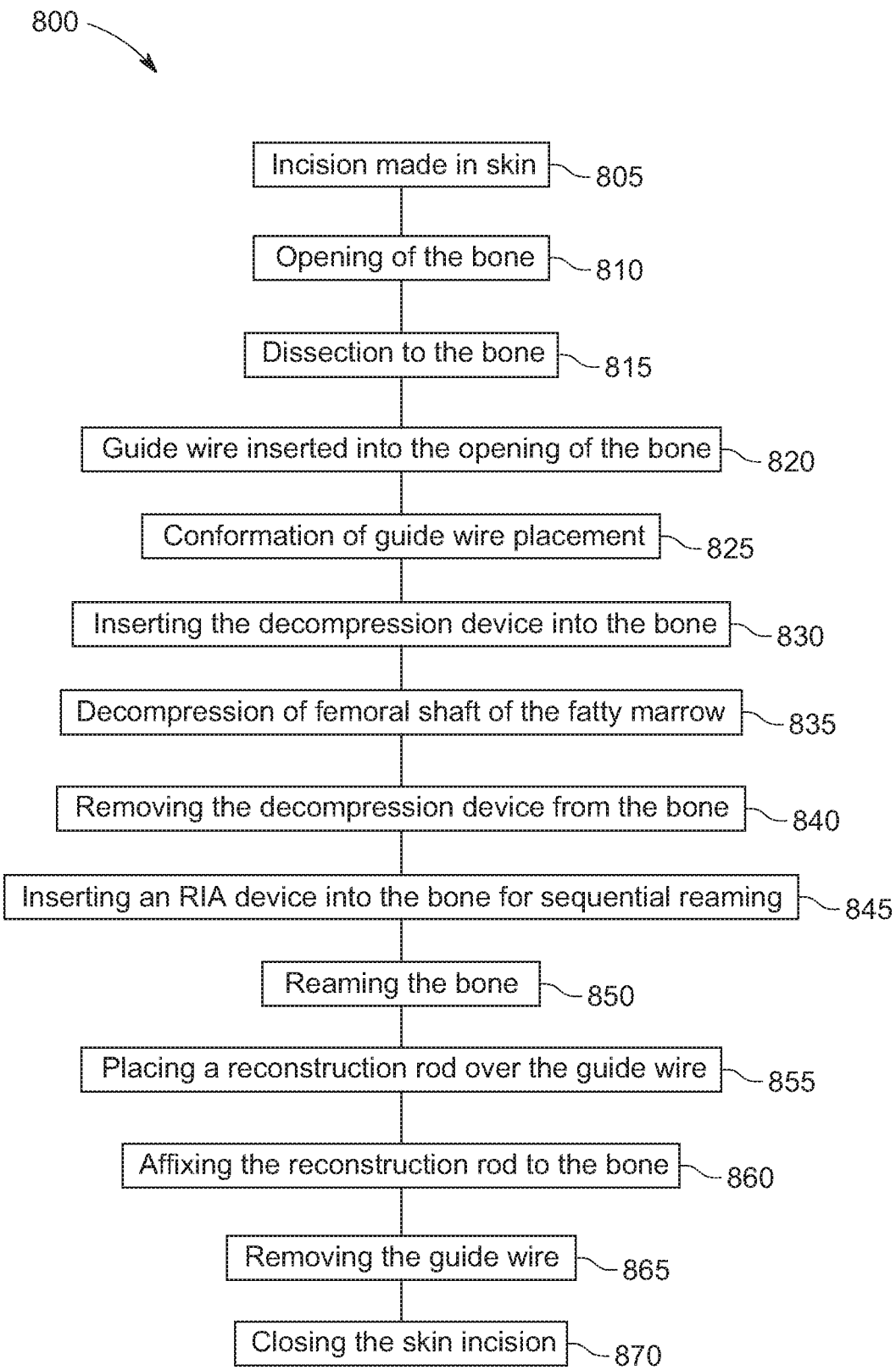

FIG. 8 shows a diagram of a method of repairing a hip fracture using the decompression device.

DETAILED DESCRIPTION OF THE INVENTION

Reference is made herein to the attached drawings. Like reference numerals are used throughout the drawings to depict like or similar elements of the femur decompression device. For the purposes of presenting a brief and clear description of the present invention, the preferred embodiment will be discussed as used for repairing a hip fracture. In the description that follows, the term "proximal," as is traditional, will refer to the incision site of the decompression device that is closest to the operator, while the term "distal" will refer to the end of the decompression device that is farthest from the incision site during operation thereof. The figures are intended for representative purposes only and should not be considered to be limiting in any respect.

Figure 1:
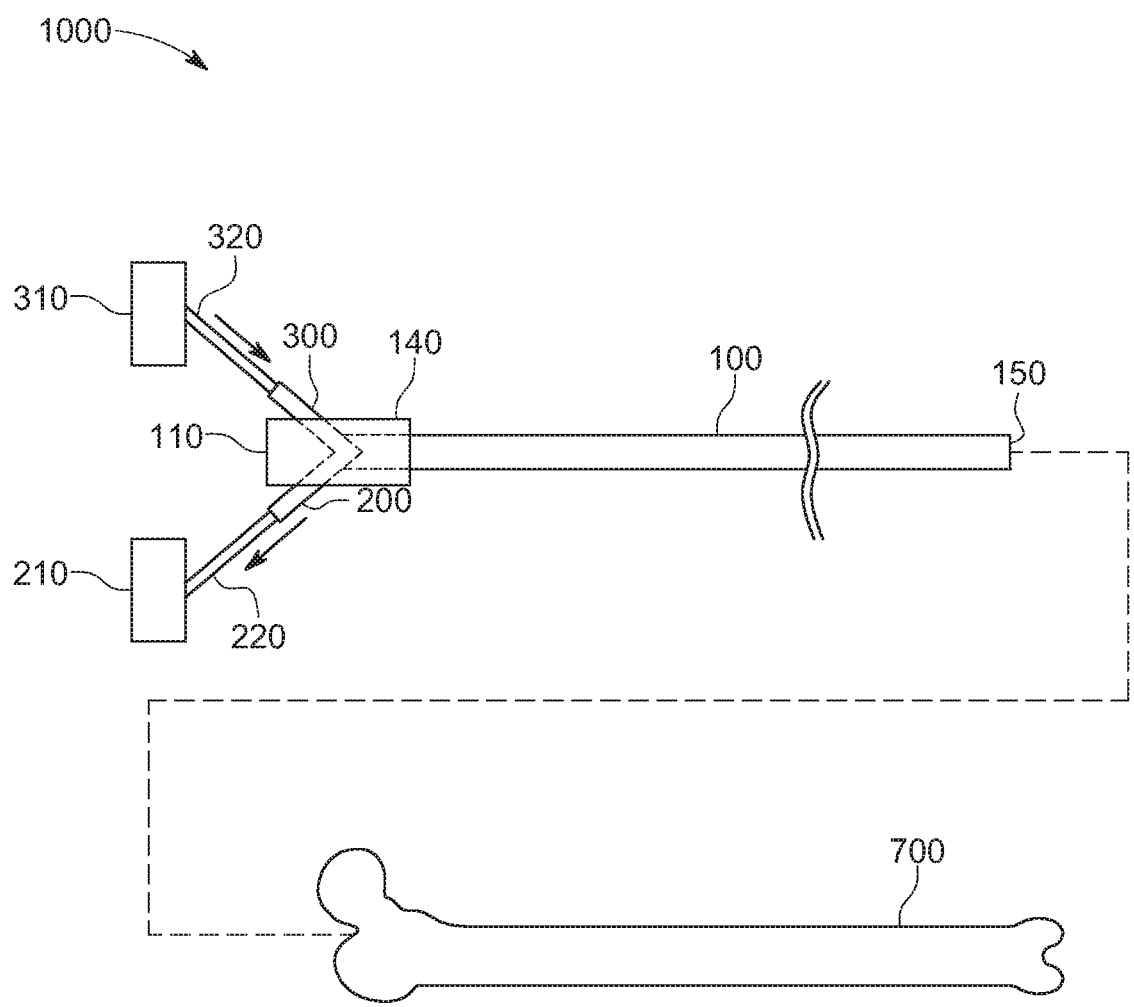
FIG. 1 shows a perspective view of an embodiment of the decompression device.

Referring now to FIG. 1 there is shown a perspective view of an embodiment of the decompression device. The decompression device 1000 provides a cannula 100, wherein the device 1000 includes a first end 110 opposite a second end 120 and channel extending therebetween. The channel (as seen in FIG. 5, 130) is in fluid communication with the first 110 and second end 120 of the device 1000 and is configured to allow fatty marrow to pass therethrough. In operation, the fatty marrow is removed using the decompression device 1000 prior to a reaming procedure used to create a space within the intramedullary canal to receive a reconstruction rod. In this way, the fatty marrow is removed prior to the reaming procedure in order to prevent excess fatty marrow from traveling to the venous system once the procedure of repairing a hip fracture is complete.

In the illustrated embodiment, the cannula 100 is composed of a hollow, semi-rigid surgical tubing and is cylindrical in shape, having a circular cross section. The cannula has a rigidity to conform to the shape of the intramedullary canal when inserted into the target bone, such as the ileac, femur, humerus, other bone, or combinations thereof. In this described embodiment, the target bone is a femur 700. The decompression device and method are used in procedures on the lower part of a body, such as during hip and knee replacements, as well as surgery of the upper body, such as during shoulder procedures. The cannula 100 extends from a handle 140 disposed at the first end of the decompression device 1000. The handle 140 provides a gripping surface to manipulate the cannula during decompression of the femur 700. In some embodiments, the cannula 100 is between 12 to 24 inches in length and 5 to 7 millimeters in diameter. The diameter and length allow the cannula 100 to be inserted into the intramedullary canal of the femur 700 and efficiently remove the fatty marrow necessary to prevent leftover fatty marrow from traveling to the venous system of the patient during the reaming procedure. In the illustrated embodiment, the depth of placement of the reconstruction rod within the femur will determine the length of cannula needed for decompression. For example, if the lowest point of the reconstruction rod will be placed half way into the femur 700, the preferred canula 100 length will be at least half the length of the femur. If the reconstruction rod will encompass the entire length of the femur, a cannula having at least a length of the femur will be needed. Generally, there is no need for a cannula to extend beyond the lowest point of the reconstruction rod position within the target bone because decompression beyond that area will not be needed. Fatty marrow is more likely to remain intact and not enter the venous system of the patient if the reconstruction rod is not being nailed to that specific portion of the target bone.

In the illustrated embodiment, the channel 130 extends through the second end 120 of the decompression device 1000 forming an open tip 150 on the cannula 100. In some embodiments, the open tip 150 comprises a flat edge. In alternative embodiments, the open tip 150 comprises a beveled, chamfered, or otherwise rounded edge that provides for penetrating the intramedullary canal.

In some embodiments, the removal of fatty marrow through the cannula 100 is facilitated by a vacuum system. In the illustrated embodiment, the vacuum system 210 removably affixes to a first port 200 extending from the first end of the decompression device 1000, wherein the first port 200 is in operable connection with the vacuum system 210. The vacuum system 210 is adapted to provide suction through the cannula 100 in order to remove the fatty marrow of the intramedullary canal when activated and inserted therein. The first port 200 is disposed at the first end 110 of the cannula 100 in order to allow the majority of the length of the cannula to remain free from projections extending outward from the decompression device 1000. In the shown embodiment, the first port 200 includes body that projects at an angle from the handle 140. The first port 200 includes a fastener for selectively forming a sealed connection with a tube of the vacuum system 210. In one use, the tube of the vacuum system 210 may be replaced with another tube or selectively attached/detached during the insertion and removal of the decompression device 1000 from the patient.

In the illustrated embodiment, a second port 300 is disposed at the first end 110 of the decompression device 1000. The second port 300 is operably connected to an irrigation source 310. The irrigation source is adapted to help prevent clogging at the open tip 150 and at one or more fenestrations (see FIG. 5), wherein the irrigation source 310 can be either a liquid or a gas. The liquid or gas enters the cannula through the second port 300 and is discharged at the second end 120 of the cannula 100. In the shown embodiment, the second port 300 is similar in shape and dimension to the first port 200, including comprising a fastener adapted to form a sealed connection. In the shown embodiment, both of the ports 200, 300 extend from the handle 140 forming an acute angle therewith, wherein the ports 200, 300 are accessible from the first end 110. In this way, fastening and unfastening of the tubes from the ports 200, 300 does not interfere with the gripping of the handle 140 and the surgical site of the patient.

In some embodiments, the decompression device consists only of the cannula having a handle extending therefrom, wherein the cannula comprises one or more fenestrations and the handle comprises the first and second port.

In some embodiments, the decompression device consists only of the cannula and a handle, wherein the first and second port extend therefrom.

Figure 2A:
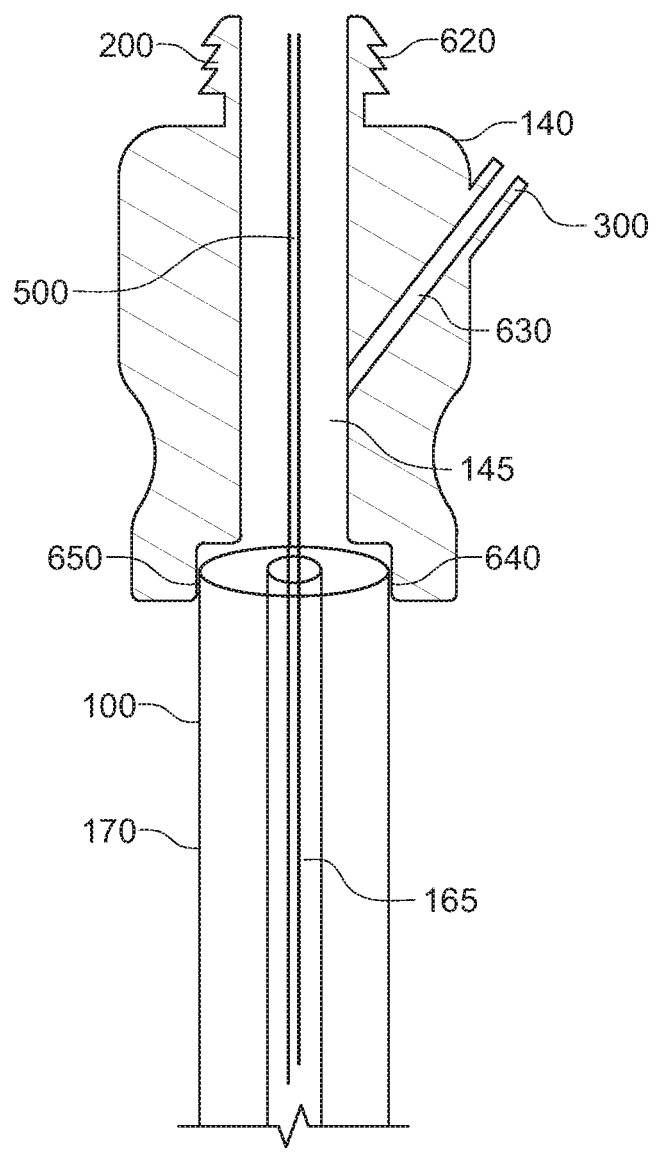
FIG. 2A shows a side cross sectional view of a first alternate embodiment of the handle and upper end of the cannula of the decompression device.
Figure 2B:
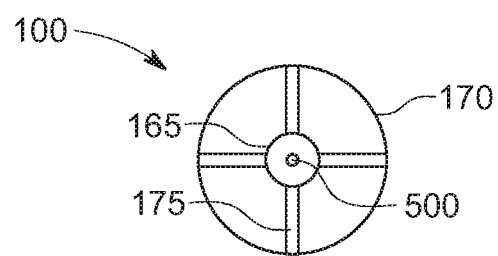
FIG. 2B shows a cross sectional view of the cannula of 2A.

Referring now to FIGS. 2A and 2B, there is shown a side cross sectional view of a first alternate embodiment of the handle and upper end of the cannula of the decompression device and a cross sectional view of the cannula of 2A, respectively. The view in FIG. 2A also illustrates the upper end of the cannula offset to the cross section of the handle so as to provide a perspective of a size and location of a guidewire being inserted into the channel of cannula. In a first alternate embodiment of the handle 140, the first port 200 is disposed at an upper end thereof. A handle channel 145 extends from the first port 200 and terminates at a recess 650 of within a lower end 640 of the handle 140. A linear handle channel 145 provides increased flow from the vacuum system and results in reduced clogging around curved choke points. In the illustrated embodiment, the recess 650 is sized to receive and secure the cannula 100 therein via a friction fit. The second port 300 extends from a sidewall of the handle 140, wherein the sidewall is perpendicular to the upper end thereof. The second port 300 is in fluid communication with the handle channel 145 via a second port channel 630. The second port channel 630 intersects the handle channel 145 within the handle 140.

In the illustrated embodiment, the cannula 100 comprises an inner diameter 165 and an outer diameter 170. The outer diameter 170 fits flush within the recess 650 and the inner diameter 165 is aligned with the handle channel 145, such that the inner and outer diameter are concentric within the cannula 100. In this way, a guide wire 500, passes through handle channel 145 and into the inner diameter 165 of the cannula 100, allowing for increased flow volume for vacuum system. A support structure 175 extends between the inner and outer diameter of the cannula and along the length thereof. In the illustrated embodiment, the support structure 175 comprises a plurality of members having voids extending therebetween. The support structure, in the illustrated embodiment, serves to maintain stability of the cannula as well as provide a cannula with a lower weight due to the absence of material within the voids. In some embodiments, the handle comprises a cutout 610 extending the entire circumference of the exterior in order to provide additional gripping comfort and surface area to the user. In the illustrated embodiment, the first port comprises a Luer taper connector 620 so as to operably connect the vacuum system thereto.

Referring now to FIGS. 3A and 3B, there is shown a side cross sectional view of a second alternate embodiment of the handle and upper end of the cannula of the decompression device and a cross sectional view of the cannula of 3A, respectively. The view in FIG. 3A also illustrates the upper end of the cannula offset to the cross section of the handle so as to provide a perspective of a size and location of a guidewire being inserted into the channel of cannula. In the illustrated embodiment, the second port channel 630 does not intersect the handle channel 145, but is parallel thereto, such that the second port channel 630 is offset. The second port 300 is adjacent to the first port 200, wherein both ports extend from the upper end of the handle 140. The opposing end of the second port channel 630 terminates at the recess 650. In the illustrated embodiment, the inner diameter 165 of the cannula is aligned with the second port channel 630, such that the guide wire 500 and irrigation are not concentric within the cannula 100 when in use.

Referring now to FIGS. 4A and 4B, there is shown a side cross sectional view of a third alternate embodiment of the handle and upper end of the cannula of the decompression device and a cross sectional view of the cannula of 4A, respectively. The view in FIG. 4A also illustrates the upper end of the cannula offset to the cross section of the handle so as to provide a perspective of a size and location of a guidewire being inserted into the channel of cannula. In a third alternate embodiment of the handle 140, the second port extends from the sidewall of the handle, but the second port channel 630 does not intersect the handle channel 145. The inner diameter 165 of the cannula 100 is aligned with the second port channel 630, such that the second port channel 630 is offset from the center of the cannula 100. In operation, the handle channel 145 is configured to receive the guide wire 500 such that the guide wire 500 does not pass through the inner diameter 165 of the cannula 100, but instead extends between the outer diameter 170 and inner diameter thereof.

Referring now to FIG. 5, there is shown a cross sectional view of a second end of an embodiment of the decompression device inserted into a femur. In some embodiments, one or more fenestrations 400 are disposed on a sidewall 160 of the cannula 100. The fenestrations 400 extend entirely through the sidewall 160 and are in fluid communication with the channel 130. The fenestrations 400 are configured to allow fatty marrow to pass therethrough during the decompression of the intramedullary canal. The fenestrations 400, cooperatively with the open tip, provide for the efficient removal of the fatty marrow and other fluid from the intramedullary canal. The fenestrations 400 are configured to only extend along the portion of the cannula 100 that is inserted within the intramedullary canal. In some embodiments, the fenestrations 400 extend along half the length of the cannula 100. For example, a cannula 24 inches in length will have fenestrations extending no more than 12 inches from the second end of the decompression device 1000. In the illustrated embodiment, the fenestrations 400 are arranged at fixed intervals about the sidewall. In some embodiments, the fenestrations 400 are disposed around the circumference of the sidewall of the cannula 100. In the illustrated embodiment, the fenestrations 400 are circular in shape. However, in alternate embodiments, the fenestrations are any suitable shape to allow fatty marrow to pass through.

In the illustrated embodiment, the fenestrations 400 are sized to prevent cancellous bone from passing through the cannula, while allowing the marrow to flow through the channel. In the shown embodiment, a first diameter 410 of each of the fenestrations 400 is greater than a first distance 420 between an outer side of the guide wire 500 positioned within a center of the cannula 100 and an inner side of the sidewall 160. In this way, the fenestrations 400 and the guide wire 500 cooperatively filters particulates through the channel 130. In one embodiment, the filtering allows for the marrow to enter the channel 130 and prevents larger cancellous particulates from entering the channel 130. In the illustrated embodiment, the first diameter 410 of each fenestration 400 is between 0.5 millimeters to 3 millimeters and the tolerance between the guide wire 500 and the sidewall 160 (first distance 420) is 1 to 2 millimeters.

Referring now to FIG. 6, there is shown a block diagram of the components of an embodiment of the decompression device. In some embodiments, the femur 700 decompression device 1000 comprises an ultrasonic transducer 440 for facilitating the fatty marrow to pass through the fenestrations or another opening disposed on the cannula 100. The ultrasonic transducer 440 is configured to vibrate the cannula 100 and surrounding particulates such that blockages are discouraged from forming. In one embodiment, the ultrasonic transducer 440 is positioned towards the second end of the device 1000 and sends the vibration waves along the length of the cannula 100. The frequency and amplitude of the ultrasonic transducer 440 is reconfigurable and may be specific for each cannula 100 having specific fenestration arrangement and dimensions.

In other embodiments, the decompression device 1000 includes a heating element 430 adapted to apply heat and further facilitate decompression. The heating element 430 is in operable connection to the cannula 100. The heating element 430 is configured to heat a portion of the cannula 100 and transmit the heat to the fatty marrow in order to lower the viscosity of the fatty marrow and allow for increased flow through the fenestrations or open tip. In the illustrated embodiment, the heating element 430 is configured to heat fatty marrow between 100 to 110 degrees F. in order to liquify the marrow.

Referring now to FIGS. 7A and 7B, there is shown a perspective view of an embodiment of the decompression device inserted through a proximal end of a femur and a perspective view of an embodiment of the decompression device inserted into a femur over a guide wire, respectively. During a hip repair procedure, an incision is made within the skin of a patient and dissected to a bone. Once the bone is accessible, an opening 710 is made into the proximal end 720 thereof via an awl or drill. A guide wire 500 is inserted into the opening and placed within the intramedullary canal 510. The guide wire 500 comprises a blunt distal end 520 having a diameter larger than the open tip of the cannula 100, such that the cannula 100 is unable to pass beyond the blunt distal end 520. In this way, the blunt distal end 520 is prevented from puncturing the sidewall of the intramedullary canal when passing therethrough. In the illustrated embodiment, the blunt distal end 520 is a metal circular member sintered to the guide wire. In some embodiments, the open tip of the cannula tapers to a diameter less than the diameter of the blunt distal end 520 of the guide wire 500.

Once the proper placement of the guide wire 500 is confirmed via an X-ray, the cannula 100 is disposed over the guide wire 500 and enters the intramedullary canal 510. The proper position of the guide wire 500 is defined as entering the distal tip on the femur. The channel 130 is configured to receive a guide wire 500, wherein the guide wire 500 is adapted to support or guide the cannula 100, having a larger diameter than the guide wire 500, into the intramedullary canal 510. In some embodiments, the cannula 100 is connected to the guide wire 500 to prevent accidental puncture into the soft tissue if the opening is missed. In the illustrated embodiment, the guide wire 500 is composed of a thin wire having a diameter of between 2 to 4 millimeters. and a length between 2-4 feet.

Once the cannula 100 is in position, the vacuum system is activated in order to create suction through the first port to remove the fatty marrow from the intramedullary canal 510. The fatty marrow is suctioned into the open tip and the fenestrations, and through the first port into a collection member via a tube operably connected to the first port. The collection member receives the fatty marrow while simultaneously allowing continuous removal thereof. In some embodiments, the vacuum system comprises a bifurcated tube extending from the first port wherein one tube is connected to the vacuum source and another tube is connected to the collection member.

In some embodiments of the decompression method, fluid or gas is introduced into the cannula 100 through the second port, wherein the vacuum system simultaneously removes the fluid or gas through the first port. This enables allows for dissolution of the fatty marrow for more efficient removal thereof. The heating element is activated in order to lower the viscosity of the fatty marrow if one or more of the fenestrations or open tip become blocked. In other methods of use, the ultrasonic transducer is used to break apart the blocked portions of the decompression device. Once the intramedullary canal is sufficiently decompressed, the decompression device is removed. In some embodiments, the guide wire 500 remains in position for the reaming procedure.

In some methods of use, the decompression device having the vacuum system remains within the intramedullary canal throughout the entire decompression procedure. There is not a need to remove and reinsert the cannula multiple times during a single procedure as a result of the vacuum system and heating element or ultrasonic transducer. In some embodiments lacking the vacuum system, the cannula is removed and inserted more than one time during the decompression procedure.

Referring now to FIG. 8, there is shown a diagram of a method of repairing a hip fracture using the decompression device. During the surgical procedure for hip fracture repair, the surgeon creates a skin incision 805 and an opening in the top of the femur bone 810 and a guide wire is placed down the length of the intramedullary canal 820. After it is confirmed that the guide wire is in a correct position 825, the decompression device is placed within the cannula prior to the reaming procedure 830. In the illustrated embodiment, the pressure of the vacuum system needed to maintain a sufficient flow rate in the system is calculated via application of Poiseuille's equation. The fatty marrow and other fluids within the intramedullary canal are sufficiently removed using the decompression device 835. The decompression device is completely removed from the intramedullary canal once the decompression has concluded 840. After the decompression device is removed, a drill or other device capable of reaming or widening the intramedullary canal, such as a RAI device, is placed therein 845 and the bone is reamed 850. Since the decompression of the intramedullary canal is performed prior to the reaming procedure, the decompression prevents excess fatty marrow from entering the venous system of the patient that can occur during the reaming and nailing procedures. Once the reaming has concluded, a femoral rod is placed over the guide wire 855 and is secured to the femur 860. The guide wire is removed 865 and the skin is closed 870. The decompression of the intramedullary canal occurring prior to the reaming thereof is a preventative step towards reducing the rate of negative patient outcomes.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A decompression device, comprising:
   a cannula having a channel in fluid communication with a first end of the cannula and a second end of the cannula, wherein the channel is configured to allow marrow to pass therethrough;
   a first port configured to be operably connected to an aspirator system;
   wherein the channel extends through the second end of the cannula forming an open tip;
   wherein the channel is configured to receive a guide wire, the guide wire configured to enter the intramedullary canal;
   wherein the aspirator system is adapted to extract the marrow of the intramedullary canal through the channel when activated and inserted therein;
   a heating element operable connected to the cannula and configured to heat fatty marrow between 100 and 110 degrees.

2. The decompression device of claim 1, wherein the first port is disposed at the first end.

3. The decompression device of claim 1, further comprising a second port configured to be operably connected to an irrigation system.

4. The decompression device of claim 3, wherein the second port is disposed at the first end.

5. The decompression device of claim 1, wherein the cannula is cylindrical.

6. The decompression device of claim 1, one or more fenestrations disposed on a sidewall of the cannula, wherein the one or more fenestrations extend entirely through the sidewall and are in fluid communication with the channel.

7. The decompression device of claim 6, wherein the one or more fenestrations are configured to allow fatty marrow pass therethrough.

8. The decompression device of claim 6, wherein the one or more fenestrations are arranged at fixed intervals about the sidewall.

9. The decompression device of claim 6, wherein a first diameter of each of the one or more fenestrations is greater than a first distance between an outer side of the guide wire and an inner side of the sidewall.

10. The decompression device of claim 1, wherein the first end of the cannula includes a handle disposed thereon.

11. The decompression device of claim 1, further comprising an ultrasonic transducer.

12. The decompression device of claim 1, wherein the aspirator system is activated via negative pressure.

13. A method for repairing a hip fracture, comprising:
   creating an opening in a proximal end of a femur;
   inserting a guide wire through the opening to a distal end of the femur;
   confirming the guide wire is disposed at the distal end;
   placing a cannula over the guide wire, wherein the cannula includes a first end and a second end;
   heating the cannula via a heating element operable connected to the cannula;
   decompressing the femur by removing marrow from the femur, wherein the fatty marrow is removed using an aspirator operably connected to the cannula;
   removing the cannula from the femoral canal;
   reaming of the femoral canal with a drill placed over the guide wire;
   placing a femoral rod over the guide wire;
   securing the femoral rod to the femur.

14. The method for repairing a hip fracture of claim 13, wherein a matrix of cancellous tissue within the intramedullary canal remains undisturbed during decompression of the femur by removing marrow from the femur.

15. The method for repairing a hip fracture of claim 13, wherein the decompression of the femur is performed prior to the reaming of the femoral canal.

16. A decompression device, comprising:
   a cannula having a channel in fluid communication with a first end of the cannula and a second end of the cannula, wherein the channel is configured to allow marrow to pass therethrough;
   a first port configured to be operably connected to an aspirator system;
   wherein the channel extends through the second end of the cannula forming an open tip;
   wherein the channel is configured to receive a guide wire, the guide wire configured to enter the intramedullary canal;
   wherein the aspirator system is adapted to extract the marrow of the intramedullary canal through the channel when activated and inserted therein;
   one or more fenestrations disposed on a sidewall of the cannula, wherein the one or more fenestrations extend entirely through the sidewall and are in fluid communication with the channel;

wherein a first diameter of each of the one or more fenestrations is greater than a first distance between an outer side of the guide wire and an inner side of the sidewall.

* * * * *